(12) United States Patent
Langeland

(10) Patent No.: US 6,936,283 B2
(45) Date of Patent: Aug. 30, 2005

(54) COMPOSITION FOR STIMULATION OF SPECIFIC METALLO-ENZYMES

(76) Inventor: Bjørn T. Langeland, Holgerslystveien 25, N-0280 Oslo (NO)

( * ) Notice: Subject to any disclaimer, the term of this patent is extended or adjusted under 35 U.S.C. 154(b) by 24 days.

(21) Appl. No.: 10/626,541

(22) Filed: Jul. 25, 2003

(65) Prior Publication Data

US 2005/0019427 A1 Jan. 27, 2005

(51) Int. Cl.$^7$ .............................................. A61K 35/78
(52) U.S. Cl. ...................... 424/728; 424/725; 424/752; 424/756; 424/757
(58) Field of Search ................................ 424/725, 728, 424/756, 757, 752

(56) References Cited

U.S. PATENT DOCUMENTS

| | | | | |
|---|---|---|---|---|
| 6,132,727 | A | * 10/2000 | Rohde et al. | 424/728 |
| 6,497,234 | B1 | * 12/2002 | Coy-Herbert | 131/352 |
| 2003/0026858 | A1 | * 2/2003 | Park et al. | 424/728 |
| 2003/0059501 | A1 | * 3/2003 | Rivier | 426/103 |
| 2003/0064134 | A1 | * 4/2003 | Eastman, III | 426/72 |
| 2003/0138520 | A1 | * 7/2003 | Bell et al. | 526/3 |
| 2003/0180414 | A1 | * 9/2003 | Gudas et al. | 426/3 |
| 2004/0096547 | A1 | * 5/2004 | Ferruzzi | 426/72 |

FOREIGN PATENT DOCUMENTS

| | | |
|---|---|---|
| JP | 62292725 | * 12/1987 |
| WO | WO-99/61038 | * 12/1999 |

OTHER PUBLICATIONS

International Product Alert bulletin entitled "Magic Energy Kick Replenishing Drink". Aug. 7, 2000, vol. 17, No. 15, PROMT Abstract.*

Product Alert bulletin entitled "HerbaSway Kudja—Therapeutic Alcohol Stress Formula". Oct. 14, 1996, PROMT Abstract.*

* cited by examiner

*Primary Examiner*—Christopher R. Tate
(74) *Attorney, Agent, or Firm*—Young & Thompson

(57) ABSTRACT

A stable composition preferably a refreshing drink for accelerating degradation of alcohol and acetaldehyde in the body, comprises synergistic combination of caffeine, herbs and fructose. Preferably, the composition comprises, Caffeine, Guaranà caffeine, Yerba Matè, *Eleutherococcus senticous, Panax ginseng*, ginger, *Glycyrrhiza glabra* (Liquorice Root), fructose and additional ingredients (sugars, flavourings, colourings, vitamins, stabilisers, whole fruit powder and the like), and optionally ginkgo biloba.

17 Claims, 3 Drawing Sheets

COMPOSITION FOR STIMULATION OF SPECIFIC METALLO-ENZYMES

FIELD OF THE INVENTION

Figure 1:
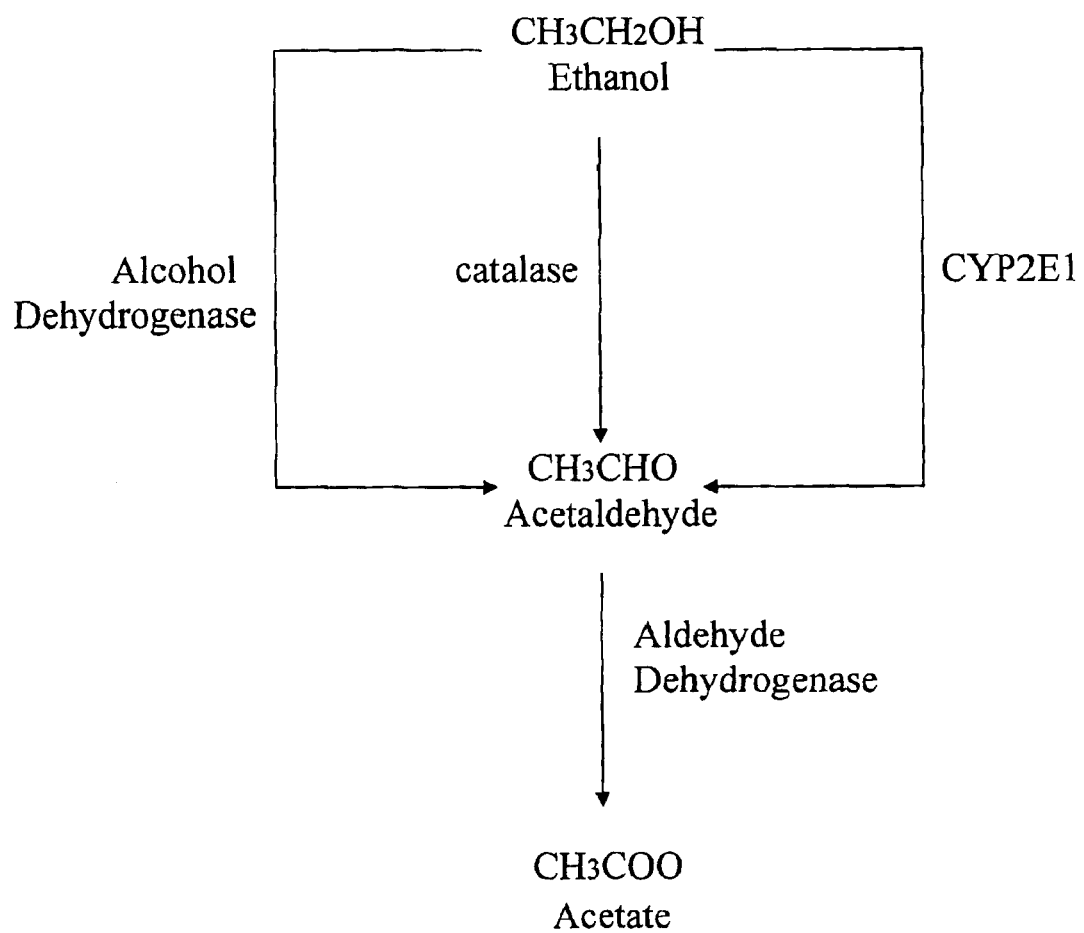
Figure 2:
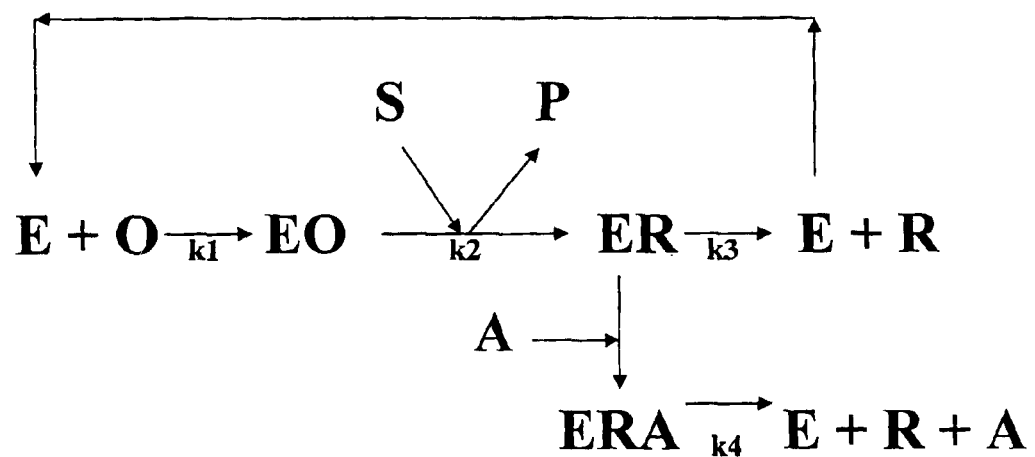

The present invention relates to a composition preferably manufactured as a beverage capable of promoting alcohol and acetaldehyde metabolism to mitigate the burden on human body, thus effective for preventing overdrunkenness, drunken sickness, and hangover.

BACKGROUND OF THE INVENTION

Consumption of alcohol may result in an accumulation of acetaldehyde, making individuals suffering from associated headaches, nausea, shaking and vertigo. This is typically termed a hangover. A number of products are known in the art, which can be taken to relieve the symptoms of a hangover. Fructose-caffeine-vitamin C and fructose-caffeine mixtures are examples of such products. Generally such products are in powder or tablet form and are added to water to provide a rehydration product for an individual to drink. These products invariably contain an analgesic, such as paracetamol or aspirin, to provide relief from pain. Products containing antihistamines, like Zyrtec, are also frequently used to combat hangover symptoms. Moreover, it may be undesirable to use analgesic and antihistamines in this manner. For instance aspirin can exacerbate some of the problems associated with alcohol consumption, such as gastrointestinal bleeding.

WO 9961038 is one example of such products, containing several of the ingredients found in the present invention. The composition described in WO 9961038 claim to have a nutritionally beneficial substituent and a substituent to stimulate short/ or long term psychological feedback and to vehicles or devices that accomplish the delivery of the nutritionally beneficial substituent to a recipient. This composition is not formulated for promoting alcohol metabolism, and also contains several components previously shown to strongly inhibit alcohol metabolizing enzymes. This is particular the case for thiol components like cysteine, acetylcysteine, glutathione and methionine, [1] which inhibit the activity liver alcohol dehydrogenase (LADH) enzyme (Ki in the uM-mM area). This is also the case for several of the heterocyclic reagents found in this composition [2, 3].

More important, the composition described in WO 9961038 also lack at least three components which is of outmost importance for the promoting effect of the present invention on alcohol metabolism. These are Yerba Matè, *Eleutherococus senticocus* and *Glycyrrhiza glabra*. These are components that are essential in the synergistic combinations responsible for stimulating the alcohol and acetaldehyde metabolizing enzymes. Experiments have shown that the absence of each of these components leads to a decrease in the synergistic—and overall effect with 30–50% and 15–25%, respectively. It should also be mentioned that Yerba Matè is added not merely for its natural caffeine content, but also for its content of several other potentially active ingredients as listed in Table 1.

W098/32434 describes a new analgesic composition of acetaminophen targeting decreasing of liver toxicity and releasing of hangover, which comprises aspartic acid promoting alcohol metabolism and methionine alleviating liver toxicity of acetaminophen.

GB 2308810 describes a fructose containing, analgesic free composition for rehydrating or preventing dehydration of an individual. By doing this, the composition is also claimed to treat hangovers caused by dehydration, physical exertion or diarrhoea.

JP 0601474 describes a product capable of promoting alcohol metabolism containing, as active ingredients, a glucoside of quercetin, divalent metallic ion and liquorice extract.

The novelty of the present invention, compared to prior art, is as mentioned above combination of special ingredients working synergistically. This is especially the case for Yerba Matè, *Panax ginseng*, ginkgo biloba, *Eleutherococus senticocus*, ginger and *Glycyrrhiza glabra* (Liquorice Root). Several of these ingredients could be found in the above-mentioned prior art, but not in the necessary combinations to obtain significant synergetic effects. The novel combinations of the present invention were found through a significant number of inclusion/exclusion experiments. The results from these experiments showed surprisingly that an especially effective combination to prevent hangover (and for increased energy level) was Yerba Matè, *Panax ginseng* and ginkgo biloba and that the synergistically effect was much greater than a mere additative effect. Another novel combination was *Eleutherococus senticocus*,ginger and *Glycyrrhiza glabra* (Liquorice Root), which were found to significantly increase the activity of alcohol metabolizing enzymes.

A highly specific composition is provided giving a significantly higher alcohol- and acetaldehyde degradation than any of the above mentioned products as well as existing fructose-vitamin C and fructose-caffeine mixtures. It is free of enzymes and NADH/NAD (nicotinamide adenine dinucleotide), which would reduce the stability of the product, and free of compounds harmful to health. The caffeine variants, the herbs and fructose have a synergistic effect.

It is an object of the present invention to obviate and/or mitigate the above disadvantages by providing a composition suitable for accelerating alcohol and acetaldehyde metabolism to reduce/prevent alcohol related damages and hangover symptoms.

SUMMARY OF THE INVENTION

The present invention is a stable composition preferably a refreshing drink for accelerating degradation of alcohol and acetaldehyde in the body, comprising synergistic combination of caffeine, herbs and fructose, a preferred embodiment comprises, Caffeine, Guaranà caffeine, Yerba Matè, *Eleutherococcus senticous, Panax ginseng*,ginger, *Glycyrrhiza glabra* (Liquorice Root), fructose and additional ingredients (sugars, flavourings, colourings, vitamins, stabilisers, whole fruit powder and the like), and optionally ginkgo biloba.

BRIEF DESCRIPTION OF THE FIGURES AND TABLES

FIG. 1.

The basic pathway of ethanol metabolism.

Alcohol converted to acetaldehyde by three enzymes; Alcohol Dehydrogenase,

Catalase and CYP 2E1.

Acetaldehyde converted to acetate by Aldehyde Dehydrogenase.

FIG. 2.

Proposed mechanism for stimulation of alcohol and/or acetaldehyde degradation.

Stimulation due to an activator forming a ternary enzyme-NADH-activator complex being more labile than the normally rate determining enzyme-NADH product dissociation.

E=enzyme; liver Alcohol Dehydrogenase or Aldehyde Dehydrogenase.
O=NAD (oxidized form of the coenzyme)
S=substrate; alcohol or acetaldehyde
P=product; acetaldehyde or acetate
R=NADH (reduced form of the coenzyme)
A=activator; caffeine variants and/or herbs
$k_3$=rate determining step
FIG. 3.
Interaction between ethanol metabolism by LADH and mitochondrial respiration.
Ethanol is oxidized to acetaldehyde by LADH (a), with concomitant reduction of NAD to NADH. NADH is then reoxidized to NAD in the mitochondria (c) by the electron transport chain (d), and oxygen is consumed (g). Substances that are phosphorylated with concomitant formation of ADP from ATP (f) increase electron flux through the respiratory chain (e), with a subsequent increase in oxygen consumption and rates of NADH reoxidation.

TABLE 1

Composition of Yerba Maté.

Studies show that the Yerba Mate has the following components:
Water, cellulose, gums, dextrin, mucilage, glucose, pentose, fat substances, aromatic resin, legumin, albumin, xanthine, theophylline, caffearin, folic acid, caffeic acid, viridic acid, chlorophyll, cholesterin and essence oil.
Ashes contain great amounts of potassium, lithium, folic, sulfuric, carbon, chloric and citric acids, beside magnesium, manganese, iron, aluminum and arsenic traces.
Xanthine, theophylline and theobromine are three strongly related alkaloids found in Yerba Mate and are some of the most interesting compounds from a therapeutic standpoint. The Yerba Mate's xanthine rate averages 1.60%, whereas it is 1.10% in infusions.

TABLE 2

The effect of the composition of the present invention on alcohol metabolism and hangover symptoms.

Alcohol was consumed as vodka mixed with Sprite (The Coca Cola Company), and drunk within one hour. The alcohol level (measured in ‰) was measured with a CA 2000 Digital Alcohol Detector once every 30 minutes. Each value is an average of four parallel measurements.
Evaluation of effect against hangover was graded on a scale from 1–10 (where 10 is the highest score). 10 healthy individuals;
6 males and 4 females attended the study.
A) 500 ml of the composition according to the invention was consumed 30–60 minutes after alcohol consumption.
B) 500 ml of an solution containing 90 g fructose, 90 mg caffeine and 500 mg vitamin C was consumed 30–60 minutes after alcohol consumption

TABLE 3

The effect of a fructose-free composition on alcohol metabolism and hangover symptoms.

2 cl of a fructose-free composition were consumed 30 minutes after alcohol consumption.
Experimental procedures equal to those in Table 2 A and B.

DETAILED DESCRIPTION OF THE INVENTION

The present invention is a stable composition preferably a refreshing drink for accelerating degradation of alcohol and acetaldehyde in the body, containing synergistic combination of caffeine, herbs and fructose.

The present invention finds application, for example, in reducing/preventing the onset of symptoms associated with a hangover in an individual. The composition may also be taken to obtain lower alcohol levels in the blood the day after alcohol consumption. The composition will also in part reduce/prevent dehydration. In the case of preventing the onset of symptoms associated with hangover the composition can be taken immediately after alcohol consumption. By accelerating the key enzymes of alcohol metabolism, alcohol and acetaldehyde degradation will increase and suppress the undesirable effects of excessive alcohol consumption (e.g. headache, cardiovascular disorders, thirst, nausea, shaking, vertigo, fatigue and coordination difficulties).

The present invention therefore provides a composition suitable for use in:
  Reducing/preventing the onset of symptoms associated with hangover,
  Accelerating alcohol degradation
  Reducing/preventing dehydration The composition of the present invention may also be taken to provide an increased energy level in an individual after physical exertion due to exercising or illness. Individuals travelling for long periods of time, such as on long haul aircraft flights can also become exerted and dehydrated, particularly due to alcohol consumption and may therefore also benefit from taking the composition.

The composition of the present invention may in addition also have some medical applications:
  Treatment of acute alcohol poisoning.
  Increasing the rate of alcohol (and possibly acetaldehyde) degradation, it could also be used to depress cell and tissue damages caused by these highly reactive reagents.
  Possible reduction of the intoxicating ethanol effects may also make this composition suitable for depressing the craving for alcohol in alcoholics.
  If the acceleration of alcohol degradation exceeds the acceleration of acetaldehyde degradation, the present invention could also find applications in enhancing the effect of drugs like disulfiram. Then, by reduction of the needed drug dose, side effects and drug toxicity may be depressed or removed.

The composition of the present invention may also contain a number of additional ingredients such as green tea, additional sugars, flavourings, colourings, vitamins, stabilisers, whole fruit powder and the like. It is also possible to add analgesics to the composition.

Preferably the composition dissolved in water or other suitable liquid can be made effervescent typically by carbonation using e.g. carbon dioxide.

The composition may also be formulated as a dry powder, a mixture, a syrup, granules, tablets, and sachets forms. The composition of the present invention may in addition be formulated to a pharmaceutical preparation. Where appropriate this pharmaceutical additionally comprises a pharmaceutically compatible carrier. Suitable carriers and the formulation of such pharmaceuticals are known to a person skilled in the art.

Composition

The amount of each component in the composition is independently selected, depending on the particular application the composition is to be used for. In a preferred embodiment of the present invention the composition comprises: Caffeine (0.001–0.1%, preferably 0.01%), Guaraná caffeine (0.001–0.1%, preferably 0.01%), Yerba Matè (0.001–0.1%, preferably 0.01%), *Eleutherococcus senticous* (0.05–2.0%, preferably 0.2%), *Panax ginseng* (0.002–0.2%, preferably 0.02%), ginger (0.3–30%, preferably 3.0%), *Glycyrrhiza glabra* (Liquorice Root) (0.02–2.0%, preferably 0.2%), ginkgo biloba (0.00–0.2%, preferably 0.02%), and optionally fructose (0–99%, preferably 75%). Additional ingredients (sugars, flavourings, colourings, vitamins, stabilisers, whole fruit powder and the like) (0.1–89.5%, preferably 21.5%). The above percentages are all percentage/dry weight of the composition.

The composition is preferably dissolved in water or other suitable liquid to provide the aqueous composition. Preferably the composition is dissolved in the ratio of 1 part composition to 10 parts water/suitable liquid, more preferably 1 part composition to 5 parts water/liquid. Typically a preferred amount for an individual is between 250–750 ml of the aqueous composition, more preferably 400–500 ml. The pH of the aqueous composition is about 3–7.5, more preferably 3–5.5. A method is provided for producing the composition of the present invention. The method of the present invention comprises:

a) mixing the fructose and the dry components soluble in water (i.e. caffeine, *Eleutherococus senticocus* and *Glycyrrhiza glabra* (Liquorice root), b) adding water to the dry mixture in a) in a ratio of 1:2 (dry mixture: water), c) stirring the mixture until all components are dissolved, d) adding the ingredients (Guaraná, Yerba Matè, ginger, *Panax ginseng* and optionally ginkgo biloba, e) stirring the mixture until a homogenous mixture is obtained, f) adding aromatic, flavouring and/or stabilising agents, g) diluting the mixture with water (optional) until an optional volume is obtained and optionally, h) adding a colouring component to the mixture obtained in a)–e) or/and i) adding a gas, preferably carbon dioxide, to the mixture obtained in a)–e) in order to give the mixture an effervescent characteristic.

Mechanism of Action

The basic pathways of ethanol metabolism [4] are shown in FIG. 1. The effect of the composition mentioned above on stimulation of ethanol degradation and prevention of hangover are shown in Table 2. The table also depicts a comparison between the invention (Table 2A) and a fructose-caffeine-vitamin C drink (Table 2B).

The effect of the composition was a 40–90% increase in alcohol degradation and a significant reduction of hangover symptoms in every case studied. The accelerated alcohol degradation is probably due to caffeine variants and/or herbs forming ternary enzyme-NADH-activator (ERA) complexes being more labile than the normally rate limiting enzyme-NADH (ER) dissociation. The proposed mechanism is similar to that previously described for 2,2'- and 4,4'-dipyridyl [5]. The accelerated alcohol degradation may also in part be due stimulation of Catalase and/or CYP2E1,which are also involved in alcohol metabolism [6].

As accumulation of acetaldehyde is the main cause of hangover symptoms [7, 8], the effect of the composition on hangover also indicates a stimulation of Aldehyde Dehydrogenase activity. The necessary increase in acetaldehyde degradation may also in part be covered by stimulated LADH, which is also capable of aldehyde oxidation [9].

Figure 3:
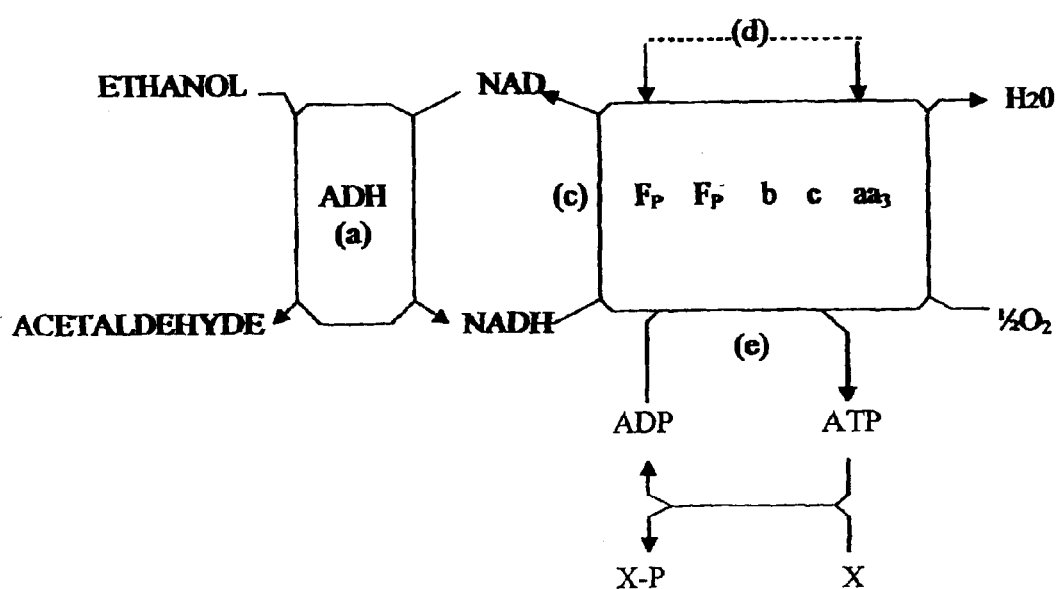

The effect of fructose on ethanol metabolism has been discussed for decades. The variety of conclusions on the effect may be due to differences in experimental design [10]. Although studies indicate that fructose alone can stimulate ethanol degradation, the effect of the composition mentioned above is due to synergetic effects of the sugar and the other activators. This is also shown by the results in Table 2, where the effects of the fructose-caffeine-vitamin C are significantly less compared to the effects of the invention. The effect of fructose is probably due to its ability to increase ATP turnover thus making more ADP available for NADH reoxidation (FIG. 3). As NADH is a strong inhibitor ($K_i$=56 $\mu$M) of LADH [6], accelerated NADH reoxidation may lead to less inhibition of LADH activity.

The novelty of this invention, compared to prior art, is the combination of ingredients working synergistically. This especially for Yerba Matè, *Panax ginseng*, ginkgo biloba, *Eleutherococus senticocus*, ginger and *Glycyrrhiza glabra* (Liquorice Root). Several of these ingredients could be found in the above-mentioned prior art, but not in the combinations to obtain significant synergetic effects. The novel combinations of the present invention were found through a significant number of inclusion/exclusion experiments. The results from these experiments showed surprisingly that an especially effective combination to prevent hangover (and for increased energy level) was Yerba Matè, *Panax ginseng* and ginkgo biloba and that the synergistically effect was much greater than a mere additative effect. Another novel combination was *Eleutherococus senticocus*, ginger and *Glycyrrhiza glabra* (Liquorice Root), which were found to significantly increase the activity of alcohol metabolizing enzymes.

The result from the experiments presented in the Example and Table 2 clearly shows that although the fructose-caffeine-vitamin C drink to a certain degree is able to accelerate alcohol metabolism and reduce hangover symptoms, the effect of the present invention is far better in all matters.

EXAMPLE

A particularly preferred formulation of an analgesic free composition embodying the present invention comprises 35 mg caffeine, 28 mg Guaraná caffeine, 27 mg Yerba Matè, 360 mg *Eleutherococcus senticous*, 70 mg *Panax ginseng*, 360 mg *Glycyrrhiza glabra* (Liquorice Root), 1 g ginger and 90 g of fructose. Natural orange flavouring is then added, and the composition is diluted to a total volume of 500 ml with water. The solution is then carbonated to provide the final composition.

When taken 30–60 minutes after alcohol consumption, the above composition has been found to be particularly efficacious in accelerating alcohol degradation and reducing/preventing the symptoms associated with a hangover.

The study presented in Table 2 and 3 included 10 individuals (6 males and 4 females, 24–57 years old).

In the first study (Table 2A) the test persons were given 8 oz. (ca.2.4 dl) of vodka mixed with 6 dl Sprite (The Coca Cola Company). The alcohol was consumed within one hour. 45 minutes after alcohol consumption each person drank 500 ml water. The alcohol level was then measured as described under.

One week later, the same test persons were given the same amount of vodka and Sprite. 45 minutes after alcohol consumption each test person drank 500 ml of the composition of the present invention. The alcohol level was then measured as described under.

Both part of the second study (Table 2 B) was performed in the same way as described for the study presented Table 1 A, with the exception that the test persons were given a 500 ml solution containing 90 g fructose, 90 mg caffeine and 500 mg vitamin C instead of the composition of the present invention. The alcohol level was again measured as described below.

The alcohol level (measured in ‰) was measured with a CA 2000 Digital Alcohol Detector once every 30 minutes in each experiment. Each value is an average of four parallel measurements. Evaluation of effect against hangover was graded on a scale from 1–10 (where 10 is the highest score).

Results

The results from the first study are shown in Table 2A. In each case the consumption of 500 ml of the composition of the present invention resulted in a markedly increase of alcohol degradation. The increase was between 67 and 92%, with an average of 83%. Hangover symptoms, as graded on a scale from 1–10 (equal to 10–100% reduction in hangover symptoms) were also markedly (80–100%) reduced.

The results from the comparing study (Table 2B), shows a much more moderate increase in alcohol degradation and reduction of hangover symptoms after consumption of a fructose-caffeine-vitamin C drink.

The increase in alcohol degradation was between 29 and 56%, with an average of 45%. The reduction of hangover symptoms was between 50 and 70%.

It is evident from the above results that composition of the subject invention is a especially effective combination to prevent hangover (and for increased energy level) Working synergistically the effect was much greater than a mere additative effect.

The above example can easily be modified to include, antimicrobials, vitamins, colouring agents and their like. The composition could also be formulated using naturally effervescent spring water, thus removing the requirement to carbonate the composition. The above composition provides an orange flavoured drink for an accelerated alcohol degradation and reduced hangover. Alternative formulations for citrus drink and lemon and lime drink contain the same principal components in like amounts, but comprise different flavourings/colourings.

While the invention has been described in connection with specific embodiments thereof, it will become apparent to those skilled in the art that various modifications to the composition and/or further applications can be envisaged.

Experiments with a Fructose-free Composition

The volume of the composition described in the example section is relatively high. This is due to the fructose content. In order to minimize the necessary volume of composition, a new set of experiments was therefore performed.

Using the same conditions described in the previous experiments (and Table 2), the same test persons was given a 2 centilitre composition containing; 5 mg caffeine, 85 mg Guaranà caffeine, 10 mg Yerba Matè, 360 mg *Eleutherococcus senticous*, 70 mg *Panax Ginseng,* 360 mg *Glycyrrhiza glabra* (Liquorice Root), 100 mg ginkgo biloba and 1 g ginger.

When taken 30 minutes after alcohol consumption, this composition was found to accelerate alcohol degradation by an average of 60% as shown in Table 3.

The results indicate the contribution of fructose to the acceleration of alcohol degradation to be approximately 20–25%. This is in good agreement with previous results [10].

Although the total effect on alcohol degradation is somewhat reduced, this new composition has several advantages compared to the fructose containing composition:

The significantly reduced volume makes it much easier to consume. This may be especially important in cases of acute alcohol poisoning.

Any negative effect caused by consuming high dosages of fructose is eliminated.

Any possible negative long-term effect of fructose on the liver is eliminated.

Fructose intolerant persons may also benefit from the use of the composition.

Combined, these advantages make the fructose-free version of the invention the most preferable. Nevertheless, dependent on wanted taste and/or volume, fructose could be added either as a sweetener or to enhance the effect on alcohol degradation.

REFERENCES

1) Langeland, B. T., Morris, D. L. and McKinley-McKee, J. S. (1999) Comp. Biochem. Biophys. Part B, 123, 155–162.
2) Bränden, C. I., Jörnvall, H., Eklund, H., Furugren, B. (1975) Alcohol Dehydrogenases. In Boyer, P. D. (ed). The Enzymes, Vol XIA. 3 Ed. New York and London. Academic Press; 104–190.
3) Miwa, K., Okuda, H., Ogura, K and Tadashi, W. (1987) Biochem. Biophys. Res. Com. 142, 993–998.
4) Kennedy, N. P. and Tipton, K. F. (1990) Essays in Biochem. 25, 137–194.
5) Langeland, B. T. and McKinley-McKee, J. S., (1997) Comp. Biochem. Physiol. 117, 56–61.
6) Lands, W. E. M. (1998) Alcohol. 15, 147–160.
7) Kitson. T. M. (1977) Journal of Studies on Alcohol. 38, 96–113.
8) Langeland, B. T. and McKinley-McKee, J. S., (1996) Alcohol & Alcoholism. 31, 75–80.
9) Henehan, G. T. M. and Oppenheimer, N. J. (1993) Biochemistry. 32, 735–738.
10) Cronower, B. P et al. (1986) The Journal of Pharmacology and Experimental Therapeutics. 236, 574–579.

TABLE 1

Composition of Yerba Matè.

|  | Minimum amount | Maximum amount | Average amount |
| --- | --- | --- | --- |
| Moisture | 5.36 | 9.80 | 8.17 |
| Proteins | 8.30 | 13.45 | 10.89 |
| Carbohydrates | 9.70 | 14.18 | 12.04 |
| Starch | 2.56 | 6.63 | 4.55 |
| Glucose | 1.30 | 6.14 | 3.84 |
| Fibers | 14.96 | 19.95 | 16.96 |
| Ashes | 6.310 | 7.780 | 6.910 |
| Chlorine (g) | 0.082 | 0.160 | 0.116 |
| Sulphur | 0.082 | 0.168 | 0.125 |
| Phosphorus (g) | 0.074 | 0.214 | 0.120 |
| Calcium | 0.597 | 0.824 | 0.668 |
| Magnesium (g) | 0.134 | 0.484 | 0.337 |
| Potassium (g) | 1.181 | 1.554 | 1.350 |
| Sodium (g) | 0.000 | 0.003 | 0.002 |
| Iron (mgs) % | — | 94.000 | 59.900 |
| Cuprum (mgs) | 0.600 | 1.600 | 1.260 |
| Manganese (mgs) | 30.200 | 183.000 | 133.180 |
| Caroffin (mgs) | 0.639 | 2.267 | 1.234 |
| Caroffin (vitamin A U.I.) | 1.065 | 3.779 | 2.095 |
| Thiamin (gamma) | 62.300 | 313.100 | 222.700 |
| Riboflavin | 246.000 | 573.900 | 404.300 |
| Ascorbic acid | 8.200 | 20.700 | 11.900 |

TABLE 2

A)

| | | | | Alcohol metabolism (%/hour) | | |
|---|---|---|---|---|---|---|
| Individual | Sex | Age | Weight (kg) | Without invent | With invention | Effect against hangover |
| 1 | Male | 40 | 70 | 0.15 | 0.28 | 8 |
| 2 | Male | 35 | 95 | 0.15 | 0.25 | 10 |
| 3 | Male | 29 | 85 | 0.16 | 0.30 | 10 |
| 4 | Male | 57 | 115 | 0.17 | 0.30 | 8 |
| 5 | Male | 30 | 78 | 0.14 | 0.25 | 9 |
| 6 | Male | 42 | 83 | 0.15 | 0.28 | 9 |
| 7 | Female | 33 | 63 | 0.14 | 0.25 | 10 |
| 8 | Female | 31 | 68 | 0.15 | 0.28 | 10 |
| 9 | Female | 24 | 75 | 0.13 | 0.25 | 10 |
| 10 | Female | 55 | 62 | 0.13 | 0.25 | 8 |

B)

| | | | | Alcohol metabolism (%/hour) | | |
|---|---|---|---|---|---|---|
| Individual | Sex | Age | Weight (kg) | Without fructose solution | With fructose solution | Effect against hangover |
| 1 | Male | 40 | 70 | 0.15 | 0.22 | 5 |
| 2 | Male | 35 | 95 | 0.15 | 0.21 | 7 |
| 3 | Male | 29 | 85 | 0.16 | 0.25 | 6 |
| 4 | Male | 57 | 115 | 0.17 | 0.22 | 5 |
| 5 | Male | 30 | 78 | 0.14 | 0.20 | 7 |
| 6 | Male | 42 | 83 | 0.15 | 0.22 | 5 |
| 7 | Female | 33 | 63 | 0.14 | 0.20 | 5 |
| 8 | Female | 31 | 68 | 0.15 | 0.22 | 5 |
| 9 | Female | 24 | 75 | 0.13 | 0.20 | 6 |
| 10 | Female | 55 | 62 | 0.13 | 0.19 | 6 |

TABLE 3

| | | | | Alcohol metabolism (%/hour) | |
|---|---|---|---|---|---|
| Individual | Sex | Age | Weight (kg) | Without invention | With invention |
| 1 | Male | 40 | 70 | 0.15 | 0.25 |
| 2 | Male | 35 | 95 | 0.15 | 0.23 |
| 3 | Male | 29 | 85 | 0.16 | 0.25 |
| 4 | Male | 57 | 115 | 0.17 | 0.26 |
| 5 | Male | 30 | 78 | 0.14 | 0.22 |
| 6 | Male | 42 | 83 | 0.15 | 0.24 |
| 7 | Female | 33 | 63 | 0.14 | 0.22 |
| 8 | Female | 31 | 68 | 0.15 | 0.25 |
| 9 | Female | 24 | 75 | 0.13 | 0.20 |
| 10 | Female | 55 | 62 | 0.13 | 0.21. |

What is claimed is:

1. A composition for the promotion of alcohol and acetaldehyde degradation in a subject comprising effective amount of, comprising caffeine, Guaranà, Yerba Matè, *Eleutherococcus senticous, Panax ginseng*, ginger, *Glycyrrhiza glabra*, ginkgo biloba and fructose.

2. The composition of claim 1, further comprising an analgesic.

3. The composition of claims 1, further comprising green tea.

4. A method for promoting alcohol and acetaldehyde degradation in a subject, comprising administering to said subject an effective amount of a composition according to claim 1.

5. The composition according to claim 1, where the composition is formulated as a beverage, syrup, dry powder, tablets, granules or sachets.

6. An aqueous product comprising the composition according to claim 1 and a compound to make the product effervescent.

7. An aqueous product comprising the composition according to claim 6 and carbonation.

8. A pharmaceutical product comprising the composition according to claim 1.

9. A method of producing an aqueous product comprising a composition according to claim 1 comprising:

a) mixing fructose and the dry mixture selected from the group consisting of caffeine, *Eleutherococus senticocus* and *Glycyrrhiza glabra*, in water, b) adding water to a) in a ratio of 1:2 of dry mixture:water, c) stirring the mixture until all components are dissolved, d) adding Guaranà, Yerba Matè, ginger, *Panax ginseng* and ginkgo biloba, e) stirring the mixture until a homogenous mixture is obtained, f) adding aromatic, flavouring and/or stabilising agents, g) optionally diluting the mixture until an optional volume is obtained, h) optionally adding a colouring component to the mixture obtained in a)–e), and i) optionally adding a gas to the mixture obtained in a)–e) in order to give the mixture an effervescent characteristic.

10. A method for the promotion of alcohol and acetaldehyde degradation to suppress the undesirable effects of excessive alcohol consumption and for treating the onset of symptoms associated with a hangover, comprising administering to a subject in need thereof an effective amount of a compound according to claim 1.

11. A composition comprising by percentage/dry weight:

0.001–0.1% Caffeine, 0.001–0.1% Guaranà, 0.001–0.1% Yerba Matè, 0.05–2.0% *Eleutherococcus senticosus,*

0.002–0.2% *Panax ginseng,*

0.3–30% ginger, 0.02–2.0 *Glycyrrhiza glabra,*

0.00–0.2% ginkgo biloba, and

0–99% fructose.

12. The composition according to claim 11, further comprising an ingredient selected from the group consisting of sugars, flavourings, colourings, vitamins, stabilisers, and whole fruit, wherein said ingredient is in an amount not to inhibit the activity of alcohol and/ or acetaldehyde metabolizing enzymes.

13. The composition according to claim 11 wherein said caffeine is in an amount of 0.01%, said Guaranà is in an amount of 0.0%, said Yerba Matè is in an amount of 0.01%, said *Eleutherococcus senticosus* is in an amount of 0.2%, said *Panax ginseng* is in an amount of 0.02%, said ginger is in an amount of 3.0%, said Glycyrrhiza glabra is in an amount of 0.2%, said ginkgo biloba is in an amount of 0.02%, said fructose is in an amount of 75%, wherein the remainder of the composition further comprises sugars, flavourings, colourings, vitamins, stabilisers, and/or whole fruit powder, and wherein said sugars, flavourings, colourings, vitamins, stabilisers, and/or whole fruit powder are present in an amount that does not inhibit the activity of alcohol and/or acetaldehyde metabolizing enzymes.

14. A method for the promotion of alcohol and acetaldehyde degradation in a subject comprising administering to said subject an effective amount of the composition according to claim 11.

15. A method for the promotion of alcohol and acetaldehyde degradation in order to suppress the undesirable effects of excessive alcohol consumption and for treating the onset of symptoms associated with a hangover in a subject, comprising administering to said subject an effective amount of the composition according to claim 11.

16. A method for the promotion of alcohol and acetaldehyde degradation in a subject comprising administering to said subject an effective amount of the composition according to claim 13.

17. A method for the promotion of alcohol and acetaldehyde degradation in order to suppress the undesirable effects of excessive alcohol consumption and for treating the onset of symptoms associated with a hangover in a subject, comprising a ministering to said subject an effective amount of the composition according to claim 13.

* * * * *

UNITED STATES PATENT AND TRADEMARK OFFICE
CERTIFICATE OF CORRECTION

PATENT NO.    : 6,936,283 B2
DATED         : August 30, 2005
INVENTOR(S)   : Bjorn T. Langeland It is certified that error appears in the above-identified patent and that said Letters Patent is hereby corrected as shown below:

Column 9,
Lines 52-56, should read -- A composition for the promotion of alcohol and acetaldehyde degradation in a subject comprising an effective amount of caffeine, Guaranà, Yerba Matè, Eleutherococcus senticous, Panax ginseng, ginger, Glycyrrhiza glabra, ginkgo biloba and fructose. --.

Signed and Sealed this

Fourteenth Day of February, 2006

JON W. DUDAS
*Director of the United States Patent and Trademark Office*